United States Patent [19]

Montanari et al.

[11] 4,306,945
[45] Dec. 22, 1981

[54] EXTRACTING AROMATIC HYDROCARBONS FROM MIXTURES CONTAINING SAME

[75] Inventors: Romolo Montanari, San Dona to Milanese; Sergio Antonelli, Peschiera di Borromeo, both of Italy

[73] Assignee: Snamprogetti, S.p.A., Milan, Italy

[21] Appl. No.: 923,252

[22] Filed: Jul. 10, 1978

[30] Foreign Application Priority Data

Aug. 9, 1977 [IT] Italy .................................. 26595 A/77

[51] Int. Cl.³ .................... B01D 3/06; B01D 3/40; C07C 7/00
[52] U.S. Cl. ........................................ 203/84; 203/85; 203/87; 203/88; 585/808
[58] Field of Search ............... 585/808, 807, 804, 805; 203/58, 43, 88, 84, 85, 71, 78, 87; 208/352

[56] References Cited

U.S. PATENT DOCUMENTS

| | | | |
|---|---|---|---|
| 2,936,283 | 5/1960 | Hutchings | 585/808 |
| 3,114,783 | 12/1963 | Butler et al. | 203/58 |
| 3,177,263 | 4/1965 | Francis | 585/808 |
| 3,209,047 | 9/1965 | Young | 585/808 |
| 3,325,399 | 6/1967 | Cinelli et al. | 585/805 |
| 3,520,946 | 7/1970 | Broughton | 588/808 |
| 3,632,482 | 1/1972 | Hoory et al. | 203/88 |
| 3,639,497 | 2/1972 | Martel et al. | 585/808 |
| 3,679,579 | 7/1972 | Preusser et al. | 585/808 |
| 3,694,322 | 9/1972 | Ikeda et al. | 203/88 |
| 4,081,355 | 3/1978 | Preusser | 585/808 |

*Primary Examiner*—Wilbur L. Bascomb, Jr.
*Attorney, Agent, or Firm*—Morgan, Finnegan, Pine, Foley & Lee

[57] ABSTRACT

A method for the removal of aromatic hydrocarbon from mixtures containing non-aromatic hydrocarbon by liquid-liquid extraction and extractive distillation is described. Isoenthalpic expansion of the rectification column bottom solvent stream and addition of water to the selective solvent can be used to reduce heat consumption.

28 Claims, 1 Drawing Figure

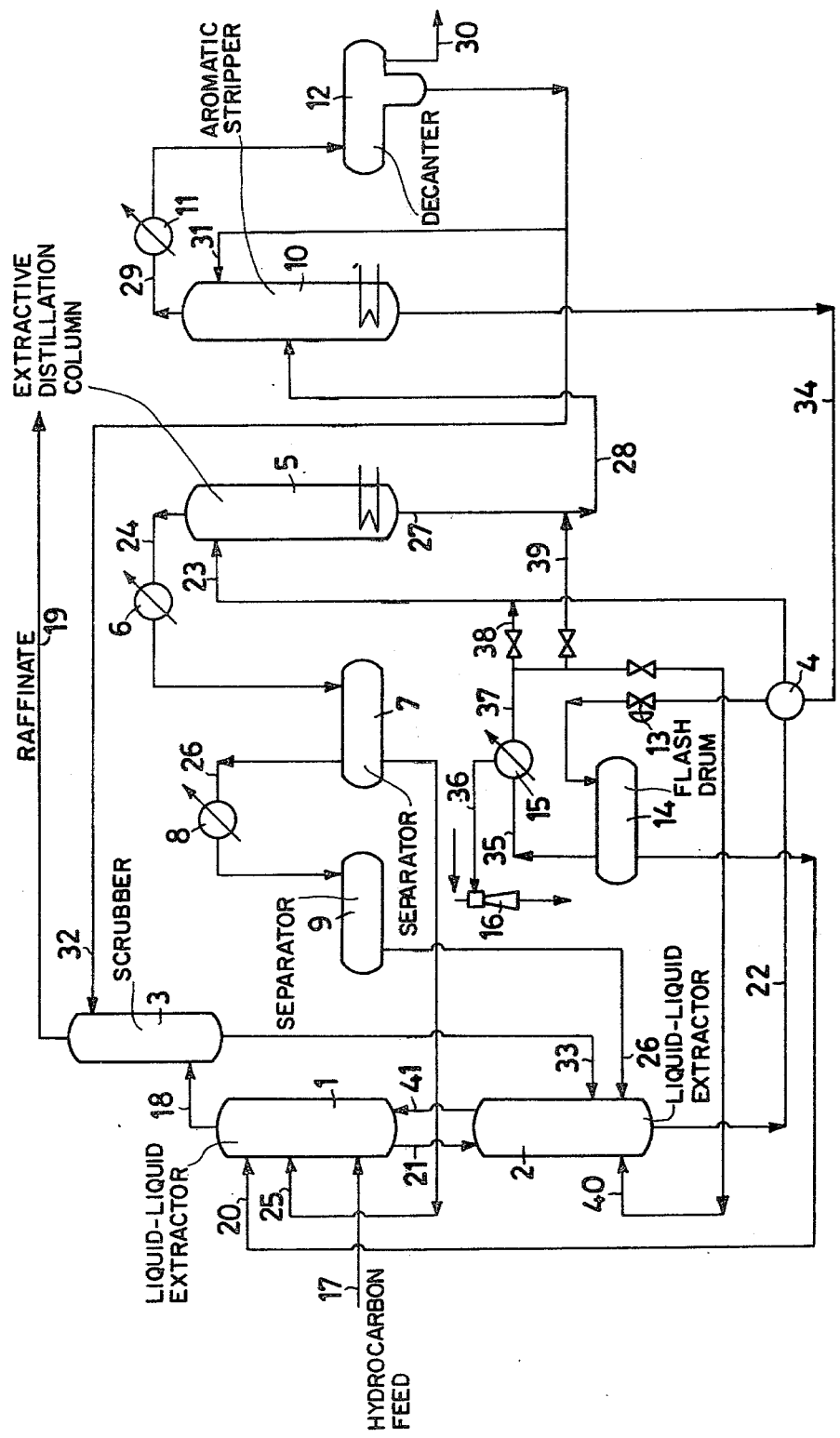

EXTRACTING AROMATIC HYDROCARBONS FROM MIXTURES CONTAINING SAME

This invention relates to a method for extracting aromatic hydrocarbons from mixtures containing them.

More particularly but not exclusively, the present invention relates to a method for extracting benzene, toluene, xylenes and other C9 from admixtures which contain them.

A number of methods are known for the extraction of aromatics in which liquid-liquid extraction followed by extractive distillation is used. In them, the extraction and extractive distillation agent is a mixture of a high-boiling solvent and water.

The high-boiling solvents which are the most suitable for these extractions are morpholine, the alkyl derivatives of morpholine, the aldehydic and ketone derivatives of morpholine. Among these, especially good results have been obtained with N-formyl morpholine. Up to 30% by weight of water is generally employed with them.

The conventional extraction and extractive distillation methods as outlined above and also one which is particularly described in U.S. Pat. No. 3,720,605 are, as a rule, comparatively expensive because of their high heat consumption. This is in large part due to the operations of extractive distillation and solvent stripping to recover the solvent for reuse in extraction and extractive distillation.

It has been found that it is possible to reduce the heat consumption by using, in the extractive distillation stage and in the rectification stages, a solvent with a higher quantity of water (in terms of the percentage of the solvent) than that utilized in past liquid-liquid extraction stage(s).

An object of the present invention is to provide a method for the extraction of aromatic hydrocarbon from a mixture containing non-aromatic hydrocarbons. The method involves:

subjecting the hydrocarbon mixture to liquid-liquid extraction in one or more series arranged columns using an extraction agent comprising an organic solvent and water to produce an overhead product and a bottoms, aromatic hydrocarbon extract;

subjecting the extract from the liquid-liquid extraction to extractive distillation to produce an overhead product and a bottoms product;

splitting the overhead product from the extractive distillation into a relatively high boiling fraction and a relatively low boiling fraction;

recycling the relatively low boiling fraction to the bottom region of the last liquid-liquid extraction column;

recycling the relatively high boiling fraction to the first liquid-liquid extraction column at a point above that at which the hydrocarbon mixture is fed;

subjecting the bottoms product from the extractive distillation to rectification to separate aromatic hydrocarbon from the organic solvent;

isoenthalpically expanding the organic solvent obtained by rectification to produce a liquid phase comprising organic solvent having a relatively lower content of water and aromatic hydrocarbon than said organic solvent separated by rectification, and a gaseous phase predominantly comprising water; and condensing the gaseous phase and employing the resulting condensate in at least one step selected from the group consisting of:

(i) recycling the condensate to a base region of the last liquid-liquid extraction column, (ii) mixing the condensate with the bottoms product of the extractive distillation, before the product is subjected to rectification, and (iii) mixing the condensate with the extract from the liquid-liquid extraction, before the extract is subjected to extractive distillation.

The percentage of water in the mixed solvent for liquid-liquid extraction is preferably from 0.5% to 12% by weight and, in the other stages is preferably from 2% to 15%. The percentage of water in the extractive distillation and solvent rectification (stripper) stages is always higher than that for extraction.

DESCRIPTION OF THE DRAWING

For a better understanding of the present invention, reference is had to the attached drawing showing a preferred embodiment of this method.

In the depicted embodiment, a charge of hydrocarbon mixture is sent via the pipe 17 to the lower portion of the liquid-liquid extractor 1. Counterflow contact takes a place in extractor 1 as solvent mixture as fed to the top portion of the extractor via the pipe 20.

From the head (or top) of the extractor 1, the raffinate or overhead product emerges and is subsequently sent, via the pipe 18, to the scrubbing column 3. There, traces of the entrained solvent are removed. This washing is carried out under counterflow conditions in scrubbing column 3 with water coming from the downstream decanting apparatus 12.

It is apparent that, the volume of wash water used in column 3 being the same, washing is the more effective for higher purity raffinate. From the top of the column 3 raffinate devoid of solvent is obtained for sending to plant department boundaries by means of pipe 19.

Water recovered from the bottom of the scrubbing column 3 is sent, via the pipe 33 to the bottom of the liquid-liquid extractor 2. The aromatic-enriched solvent exiting the bottom of the extractor 1 is fed, via the pipe 21, onto the head plate of the extractor 2. From the head plate of the extractor 2 itself, a second raffinate or overhead product is obtained. It is recycled via the pipe 41 to the bottom of the extractor 1 in order that its content of aromatic hydrocarbons may be recovered.

To the bottom of the extractor 2 are sent, via the respective pipes 33 and 26, the used washing water scrubbing exiting the column 3 and a stream of hydrocarbon and water obtained from the extractive distillation column 5 via condenser 6 and then 8.

One of the important features of this invention is to have available a stream composed predominantly by water but also including solvent and aromatic hydrocarbons, obtained from condensation in the condenser 15 of the vapor from the evacuated flash-drum 14.

Via the pipe 40 it is possible to feed a portion of such stream to the base of the extractor 2 to attain optimum water contents.

The bottom stream of the extractor 2 is sent via the pipe 22, to the heat exchanger 4. There heat is recovered from solvent exiting the bottom of the stripper 10. Raffinate or bottom product entering exchanger 4 by pipe 22 is heated and then is fed to the extractive distillation column 5 via pipe 23. Prior to intake into column 5, the enriched solvent is supplemented again with water by means of the pipe 38, the water coming from the condenser 15.

The addition of water via the pipe 38, acts favourably by facilitating the separation of the nonaromatic hydrocarbons, thus permitting a high purity aromatic extract to be obtained with diminished heat consumption relative to cases in which less water is used.

This reduction obtains because the solvent used in aromatics extraction are high-boiling in nature The higher the water content, the lower is the boiling point of the water solvent mixture concerned. The addition of water similarly reduces heat consumption during extractive distillation.

One also need only stream of solvent and extracted aromatic in pipe 27, to a low temperature. Heat is thereby saved attributable to different levels of water content, the performance of the extractive distillation column remains the same.

The head product of the extractive distillation column 5 is sent by means of the pipe 24, to the partial condenser 6. There a minimum fraction of water is caused to condense with a fraction of the heavier aromatic hydrocarbons, of the high-boiling saturated hydrocarbons and of the nonaromatic hydrocarbons which are characterized by an anomalous polarity which increases their solubility in the solvent.

Via the pipe 25, the condensate separated in separator 7 is then fed to the extractor 1, above the intake for pipe 17, so as to facilitate the venting of the anomalous polarity nonaromatic into the raffinate. This avoids both the accumulation of these compounds in the cycle and any worsening of the purity of the extract.

The vapour phase coming from the separator 7, is subsequently and completely condensed in the condenser 8 and collected in the separator 9. This condensate, which consist of water, lighter aromatic hydrocarbons and low-boiling saturated hydrocarbons, is fed to the base of the extractor 2, pipe 26.

Because of the water added at the base of the extractor 2 via the pipes 33 and 40, the nonaromatic higher-boiling compounds contained in the solvent phase will pass into the raffinate phase and they shall be replaced, partially, in the solvent phase, by the lower-boiling nonaromatic hydrocarbons: these can be more readily separated in the subsequent extractive distillation step.

The bottom stream of the extractive distillation column 5 is supplemented, via the pipe 39, by the remaining fraction of water exiting the condenser 15 and is subsequently fed to the aromatics-stripper 10.

In an embodiment of the present invention, water is added to the enriched solvent prior to the solvent entering the column 10.

The function of the aromatics-stripper 10 is to separate the aromatic hydrocarbons from the solvent. Such a separation step become more difficult the higher the boiling points of the aromatic hydrocarbons to be separated. It has been ascertained that the addition of water encourages this separation in quite surprising a way. By the method of the present invention, it is possible to operate in the four stages as represented by the operations carried out in the apparatus or steps numbered 1, 2, 5 and 10, with those contents of water most suitable for the solvent and consistent with other considerations.

The impoverished solvent exiting the stripper 10, goes, via the pipe 34, to be used in the heat exchanger 4 to preheat the charge to the extractive distillation column 5 and subsequently through the valve 13 for an isoenthalpic expansion in the chamber 14 under an appropriate degree of vacuum which is a function of the type of charge and the content of water in the solvent at the bottom of the stripper 10.

After the heat exchange in the exchanger 4, the steam from pipe 34 is at a such temperature level as not to be any longer useful. It is consequently split into two streams for pipes 35 and 20, gaseous and liquid, respectively—soenthalpic expansion at vacuum degrees which are sufficiently intense to attain 40 mmHg of absolute pressure.

The stream pipe 35 is essentially composed by water, and minor amounts of solvent and aromatic hydrocarbons, whereas the stream in pipe 20 is characterized by a relative considerable reduction of the contents of water and hydrocarbons The stream in pipe 20, by virtue of a lesser water contents and a lesser contents of residual hydrocarbons, permits liquid-liquid extractor 1 to operate under better conditions since the dosage of solvent can be reduced over that of the conventional methods. That result is a diminished heat consumption and a higher recovery of the aromatic hydrocarbons.

Likewise, the stream in pipe 35, upon subsequent condensation in the condenser 15, can be split into the streams in pipes 40, 38 and 39 to be used, as outlined above in detail, to vary the water contents at the base of the liquid-liquid extractor 2, in the extractive distillation column 5 and in the aromatics-stripper 10.

The vacuum in the separator 14 and the condenser 15 is maintained by the ejector 16.

It is important to note that the degree of vacuum to be obtained is closely connected with the desire of obtaining a complete condensation (with the exception of the uncondensables) of the in pipe stream 35 so as to avoid possible losses of aromatic hydrocarbons. The isoenthalpic expansion on the solvent mixture at the stripper bottom is such as to permit other undeniable advantages. These stem from the fact that, contrary to what is experienced with the prior art, the solvent at the stripper bottom may have a composition which is different from that of the solvent fed to the extractor 1.

These advantages include the following:

1. The residual contents of aromatic hydrocarbons in the stream of pipe 34 are considerably higher than the analogous contents in the stream of pipe 20 because, in the isoenthalpic flash, it is possible to separate a portion of these hydrocarbons in the vapour phase. As a result, the degree of fractionation to be obtained in the aromatic-stripper is not so high and a considerable savings in heat consumption can be achieved.

2. Inasmuch as the solvent mixture from the stripper bottom has higher contents of water and hydrocarbons than the stream of pipe 20, the relative boiling point temperature, the pressure being the same, is lower than that of the stream of pipe 20. Consequently, it is possible to have a lesser heat consumption which is related to the savings of the sensible heat corresponding to the temperature differential.

3. The highest temperature point is the bottom of the stripper to lower this temperature improves the stability of the solvent and supresses possible corrosion phenomena so that carbon steel can be safely used in the entire installation.

4. As fractionation is less intense, it is possible to avoid the introduction, at the stripper base, of steam produced by the vaporization of a portion of the water obtained as a distillate in the decanting apparatus 12. The heat supplied by the bottom reboiler being the same and by reducing to a minimum the rate of flow of the distillate in pipe 32 consistent with the raffinate washing requirements, it is possible to work with high reflux ratios. Less intense solvent entrainments are thus achieved.

5. By exploiting the isoenthalpic expansion, a stream essentially composed by water is produced. It may be used according to the requirements of the installation and by exploiting heat values which could not have been used otherwise, whereas in the prior art procedures the water to be used in the installation is obtained by distillation of the solvent and subsequently stripped from the hydrocarbons in the separators at the head of the extractive distillation column and the aromatics-stripper.

The operations in the several stages, according to the method of the present invention, are conducted using the temperature and water contents as specified below.

(a) The temperature in the liquid-liquid extraction stages or extractors 1 and 2 is between 15° C. and 100° C. The water contents in the extractors 1 and 2 is between 0.5% and 12% by wt, and 0.5%–8% is the preferred range for extractor 1 and from 0.5% to 12% for extractor 2.

(b) The temperature in the extractive distillation column 5 and the aromatics stripper 10 is in the range from 50° C. to 180° C. The water content is between 2% and 15%, on a weight basis.

The most appropriate water contents are selected in each case as a function of the contents of non-aromatics and the relative ratios of the aromatics in the charge or initial hydrocarbon mixture.

For illustration only, the following example is reported. It is not to be construed as a on the present invention.

EXAMPLE

Using an installation as depicted in the accompanying drawing, the charge used was a reforming gasoline having the following composition:
Benzene: 10% by wt
Toluene: 31% by wt
Xylenes: 21% by wt
—$C_9+$aromatics: 3% by wt
Non-aromatics: 30% by wt The charge was fed at a rate of flow of 100 kg an hour to the bottom plate of the liquid-liquid extraction column 1, which had 60 foraminous plates.

To the head of the column 1, N-formyl morpholine (2% solution in water and having a residual hydrocarbon content of about 1.2% by wt) was fed at a rate of flow of 370 kg an hour. Onto the 20th plate (numbered starting from the bottom) via pipe 25 the heavier fraction obtained in the first condensation stage 7 from of the head of the extractive distillation column 5 was fed at a rate of flow of 1.5 kg an hour, of which 0.25 kg an hour was water. The column 1 was maintained at a temperature between 50° C. and 60° C. From the head of the column 1, the raffinate emerged. It was sent, after washing in the column 3, to the installation department boundaries via pipe 19 at a rate of flow of 31.9 kg an hour.

Washing water from the decanting apparatus 12 and completely devoid of solvent, was fed into scrubber 3 at a rate of flow of 2.2 kg an hour and subsequently sent to the base of the liquid-liquid extractor 2.

At the base of the extractor 2, which had 20 foraminous plates, the lighter fraction of the head product of the extractive distillation column 5 was introduced via pipe 26 at a rate of flow of 28.6 kg an hour, 7.4 kg an hour of which are water.

Lastly, via the pipe 40, a stream was sent at a rate of flow of 7.8 kg an hour, 4.3 kg an hour of which are water and the remaining fraction was hydrocarbons and solvent, to the base of the extractor 2.

The bottom stream exiting the extractor 2 had a concentration of water of 4.5% by wt relative to the total mixture while water was 5.7% by wt relative to the solvent/water system.

Prior to entering the extractive distillation column 5, the bottom stream of extractor 2 was supplemented via the line 38 at a rate of flow of 5.9 kg an hour, 3.2 kg an hour of which are water.

The temperature at the bottom of the column 5 was maintained at 146° C. and the concentration of water was 3.8% by wt relative to the mixture which also included aromatic hydrocarbons and solvent. Its concentration was 4.5% by wt as related to the solvent alone.

In the example shown, the condensate obtained from the condenser 15 was split into two streams only, for pipes 40 and 38, while maintaining in the extractive distillation column the maximum concentration of water consistent with the quantities dealt with.

The bottom stream of the extractive distillation column was sent to the aromatics-stripper 10 in the head of which the aromatic hydrocarbons, 30, were obtained at a high degree of purity. The content of non-aromatic hydrocarbons was less than 400 parts per million (ppm).

Concurrently high recoveries of aromatics at the following values were obtained:
Benzene: 100%
Toluene: 99.8%
Xylenes: 97%
$C_9+$aromatics: 85%

The aqueous-phase distillate from the decanting apparatus 12 was used for washing the raffinate in scrubber 3.

The bottom product from stripper 10 was maintained at 160° C. and had a residual hydrocarbon content of 2% by wt and a water content of 3.9% by wt.

Upon isoenthalpic expansion, there was produced a solvent to be sent to the extractor 1 with a content of residual hydrocarbons of 1.2% by wt and of water of 2% by wt.

In the separator 14, as well as in the condenser 15, a pressure of 110 mmHg (absolute) was maintained.

As compared with a conventional cycle, which does not provide for the isoenthalpic expansion of the solvent at the stripper bottom, but has the same purity of aromatic hydrocarbons, the novel cycle hereof had a heat savings as high as 18% in the extractive distillation column and in the order of 20% in the aromatics stripper, higher recoveries of the aromatic hydrocarbons being concurrently obtained.

We claim:
1. A method for removing aromatic hydrocarbon from a hydrocarbon mixture additionally containing non-aromatic hydrocarbon, which process comprises:
A. subjecting said hydrocarbon mixture to liquid-liquid extraction in one or more series arranged columns using an extraction agent comprising an organic solvent and water to produce an overhead raffinate substantially free of aromatic hydrocarbons and a bottoms extract containing aromatic hydrocarbons;

B. subjecting said extract from the liquid-liquid extraction to extractive distillation to produce an overhead product and a bottoms product;
C. splitting said overhead product from the extractive distillation into a relatively high boiling fraction and a relatively low boiling fraction;
D. recycling said relatively low boiling fraction to the bottom region of the last liquid-liquid extraction column;
E. recycling the relatively high boiling fraction to the first liquid-liquid extraction column at a point above that at which the hydrocarbon mixture is fed;
F. subjecting the bottoms product from the extractive distillation to rectification to separate aromatic hydrocarbon from the organic solvent;
G. isoenthalpically expanding the organic solvent obtained by rectification to produce a liquid phase comprising organic solvent having a relatively lower content of water and aromatic hydrocarbon than said organic solvent separated by rectification, and a gaseous phase predominantely comprising water; and
H. condensing said gaseous phase and recycling said condensate to a base region of the last liquid-liquid extraction column.

2. A method according to claim 1, wherein the temperature in the liquid-liquid extraction is from 15° C. to 100° C.

3. A method according to claim 1, wherein the contents of water in the liquid-liquid extraction is between 0.5% and 12% by weight of the extractive solvent mixture and the contents of water in the extractive distillation and rectification is higher and is between 2% and 15% by weight.

4. A method according to claim 1, wherein the temperature in the extractive distillation and aromatics rectification is from 50° C. to 180° C.

5. A method for removing aromatic hydrocarbon from a hydrocarbon mixture additionally containing non-aromatic hydrocarbon, which process comprises:
A. subjecting said hydrocarbon mixture to liquid-liquid extraction in one or more series arranged columns using an extraction agent comprising an organic solvent and water to produce an overhead raffinate substantially free of aromatic hydrocarbons and a bottoms extract containing aromatic hydrocarbons;
B. subjecting said extract from the liquid-liquid extraction to extractive distillation to produce an overhead product and a bottoms product;
C. splitting said overhead product from the extractive distillation into a relatively high boiling fraction and a relatively low boiling fraction;
D. recycling said relatively low boiling fraction to the bottom region of the last liquid-liquid extraction column;
E. recycling the relatively high boiling fraction to the first liquid-liquid extraction column at a point above that at which the hydrocarbon mixture is fed;
F. subjecting the bottoms product from the extractive distillation to rectification to separate aromatic hydrocarbon from the organic solvent;
G. isoenthalpically expanding the organic solvent obtained by rectification to produce a liquid phase comprising organic solvent having a relatively lower content of water and aromatic hydrocarbon than said organic solvent separated by rectification, and a gaseous phase predominantely comprising water; and
H. condensing said gaseous phase and mixing the condensate with the bottoms product of the extractive distillation, before said product is subjected to rectification.

6. A method according to claim 5, wherein the temperature in the liquid-liquid extraction is from 15° C. to 100° C.

7. A method according to claim 5, wherein the contents of water in the liquid-liquid extraction is between 0.5% and 12% by weight of the extractive solvent mixture and the contents of water in the extractive distillation and rectification is higher and is between 2% and 15% by weight.

8. A method according to claim 10, wherein the temperature in the extractive distillation and aromatics rectification is from 50° C. to 180° C.

9. A method for removing aromatic hydrocarbon from a hydrocarbon mixture additionally containing non-aromatic hydrocarbon, which process comprises:
A. subjecting said hydrocarbon mixture to liquid-liquid extraction in one or more series arranged columns using an extraction agent comprising an organic solvent and water to produce an overhead raffinate substantially free of aromatic hydrocarbons and a bottoms extract containing aromatic hydrocarbons;
B. subjecting said extract from the liquid-liquid extraction to extractive distillation to produce an overhead product and a bottoms product;
C. splitting said overhead product from the extractive distillation into a relatively high boiling fraction and a relatively low boiling fraction;
D. recycling said relatively low boiling fraction to the bottom region of the last liquid-liquid extraction column;
E. recycling the relatively high boiling fraction to the first liquid-liquid extraction column at a point above that at which the hydrocarbon mixture is fed;
F. subjecting the bottoms product from the extractive distillation to rectification to separate aromatic hydrocarbon from the organic solvent;
G. isoehthalpically expanding the organic solvent obtained by rectification to produce a liquid phase comprising organic solvent having a relatively lower content of water and aromatic hydrocarbon than said organic solvent separated by rectification, and a gaseous phase predominantely comprising water; and
H. condensing said gaseous phase and mixing the condensate with the extract from the liquid-liquid extraction, before said extract is subjected to extractive distillation.

10. A method according to claim 9, wherein the temperature in the liquid-liquid extraction is from 15° C. to 100° C.

11. A method according to claim 9, wherein the contents of water in the liquid-liquid extraction is between 0.5% and 12% by weight of the extractive solvent mixture and the contents of water in the extractive distillation and rectification is higher and is between 2% and 15% by weight.

12. A method according to claim 9, wherein the temperature in the extractive distillation and aromatics rectification is from 50° C. to 180° C.

13. A method for removing aromatic hydrocarbon from a hydrocarbon mixture additionally containing non-aromatic hydrocarbon, which process comprises:
  A. subjecting said hydrocarbon mixture to liquid-liquid extraction in one or more series arranged columns using an extraction agent comprising an organic solvent and water to produce an overhead raffinate substantially free of aromatic hydrocarbons and a bottoms extract containing aromatic hydrocarbons;
  B. subjecting said extract from the liquid-liquid extraction to extractive distillation to produce an overhead product and a bottoms product;
  C. splitting said overhead product from the extractive distillation into a relatively high boiling fraction and a relatively low boiling fraction;
  D. recycling said relatively low boiling fraction to the bottom region of the last liquid-liquid extraction column;
  E. recycling the relatively high boiling fraction to the first liquid-liquid extraction column at a point above that at which the hydrocarbon mixture is fed;
  F. subjecting the bottoms product from the extractive distillation to rectification to separate aromatic hydrocarbon from the organic solvent;
  G. isoehthalpically expanding the organic solvent obtained by rectification to produce a liquid phase comprising organic solvent having a relatively lower content of water and aromatic hydrocarbon than said organic solvent separated by rectification, and a gaseous phase predominately comprising water; and
  H. condensing said gaseous phase and recycling portions of the resulting condensate in the two following steps:
    (i) recycling said condensate to a base region of the last liquid-liquid extraction column, and
    (ii) mixing the condensate with the bottoms product of the extractive distillation, before said product is subjected to rectification.

14. A method according to claim 13, wherein the temperature in the liquid-liquid extraction is from 15° C. to 100° C.

15. A method according to claim 13, wherein the contents of water in the liquid-liquid extraction is between 0.5% and 12% by weight of the extractive solvent mixture and the contents of water in the extractive distillation and rectification is higher and is between 2% and 15% by weight.

16. A method according to claim 13, wherein the temperature in the extractive distillation and aromatics rectification is from 50° C. to 180° C.

17. A method for removing aromatic hydrocarbon from a hydrocarbon mixture additionally containing non-aromatic hydrocarbon, which process comprises:
  A. subjecting said hydrocarbon mixture to liquid-liquid extraction in one or more series arranged columns using an extraction agent comprising an organic solvent and water to produce an overhead raffinate substantially free of aromatic hydrocarbons and a bottoms extract containing aromatic hydrocarbons;
  B. subjecting said extract from the liquid-liquid extraction to extractive distillation to produce an overhead product and a bottoms product;
  C. splitting said overhead product from the extractive distillation into a relatively high boiling fraction and a relatively low boiling fraction;
  D. recycling said relatively low boiling fraction to the bottom region of the last liquid-liquid extraction column;
  E. recycling the relatively high boiling fraction to the first liquid-liquid extraction column at a point above that at which the hydrocarbon mixture is fed;
  F. subjecting the bottoms product from the extractive distillation to rectification to separate aromatic hydrocarbon from the organic solvent;
  G. isoehthalpically expanding the organic solvent obtained by rectification to produce a liquid phase comprising organic solvent having a relatively lower content of water and aromatic hydrocarbon than said organic solvent separated by rectification, and a gaseous phase predominately comprising water; and
  H. condensing said gaseous phase and recycling portions of the resulting condensate in the two following steps:
    (i) recycling said condensate to a base region of the last liquid-liquid extraction column, and
    (iii) mixing the condensate with the extract from the liquid-liquid extraction, before said extract is subjected to extractive distillation.

18. A method according to claim 17, wherein the temperature in the liquid-liquid extraction is from 15° C. to 100° C.

19. A method according to claim 17, wherein the contents of water in the liquid-liquid extraction is between 0.5% and 12% by weight of the extractive solvent mixture and the contents of water in the extractive distillation and rectification is higher and is between 2% and 15% by weight.

20. A method according to claim 17, wherein the temperature in the extractive distillation and aromatics rectification is from 50° C. to 180° C.

21. A method for removing aromatic hydrocarbon from a hydrocarbon mixture additionally containing non-aromatic hydrocarbon, which process comprises:
  A. subjecting said hydrocarbon mixture to liquid-liquid extraction in one or more series arranged columns using an extraction agent comprising an organic solvent and water to produce an overhead raffinate substantially free of aromatic hydrocarbons and a bottoms extract containing aromatic hydrocarbons;
  B. subjecting said extract from the liquid-liquid extraction to extractive distillation to produce an overhead product and a bottoms product;
  C. splitting said overhead product from the extractive distillation into a relatively high boiling fraction and a relatively low boiling fraction;
  D. recycling said relatively low boiling fraction to the bottom region of the last liquid-liquid extraction column;
  E. recycling the relatively high boiling fraction to the first liquid-liquid extraction column at a point above that at which the hydrocarbon mixture is fed;
  F. subjecting the bottoms product from the extractive distillation to rectification to separate aromatic hydrocarbon from the organic solvent;
  G. isoehthalpically expanding the organic solvent obtained by rectification to produce a liquid phase comprising organic solvent having a relatively lower content of water and aromatic hydrocarbon than said organic solvent separated by rectification, and a gaseous phase predominantely comprising water; and H. condensing said gaseous phase and recycling portions of the resulting condensate in the two following steps:
   (ii) mixing the condensate with the bottoms product of the extractive distillation, before said product is subjected to rectification, and
   (iii) mixing the condensate with the extract from the liquid-liquid extraction, before said extract is subjected to extractive distillation.

22. A method according to claim 21, wherein the temperature in the liquid-liquid extraction is from 15° C. to 100° C.

23. A method according to claim 21, wherein the contents of water in the liquid-liquid extraction is between 0.5% and 12% by weight of the extractive solvent mixture and the contents of water in the extractive distillation and rectification is higher and is between 2% and 15% by weight.

24. A method according to claim 21, wherein the temperature in the extractive distillation and aromatics rectification is from 50° C. to 180° C.

25. A method for removing aromatic hydrocarbon from a hydrocarbon mixture additionally containing non-aromatic hydrocarbon, which process comprises:
   A. subjecting said hydrocarbon mixture to liquid-liquid extraction in one or more series arranged columns using an extraction agent comprising an organic solvent and water to produce an overhead raffinate substantially free of aromatic hydrocarbons and a bottoms extract containing aromatic hydrocarbons;
   B. subjecting said extract from the liquid-liquid extraction to extractive distillation to produce an overhead product and a bottoms product;
   C. splitting said overhead product from the extractive distillation into a relatively high boiling fraction and a relatively low boiling fraction;
   D. recycling said relatively low boiling fraction to the bottom region of the last liquid-liquid extraction column;
   E. recycling the relatively high boiling fraction to the first liquid-liquid extraction column at a point above that at which the hydrocarbon mixture is fed;
   F. subjecting the bottoms product from the extractive distillation to rectification to separate aromatic hydrocarbon from the organic solvent;
   G. isoehthalpically expanding the organic solvent obtained by rectification to produce a liquid phase comprising organic solvent having a relatively lower content of water and aromatic hydrocarbon than said organic solvent separated by rectification, and a gaseous phase predominately comprising water; and
   H. condensing said gaseous phase and recycling portions of the resulting condensate in the three following steps:
      (i) recycling said condensate to a base region of the last liquid-liquid extraction column,
      (ii) mixing the condensate with the bottoms product of the extractive distillation, before said product is subjected to rectification, and
      (iii) mixing the condensate with the extract from the liquid-liquid extraction, before said extract is subjected to extractive distillation.

26. A method according to claim 25, wherein the temperature in the liquid-liquid extraction is from 15° C. to 100° C.

27. A method according to claim 25, wherein the contents of water in the liquid-liquid extraction is between 0.5% and 12% by weight of the extractive solvent mixture and the contents of water in the extractive distillation and rectification is higher and is between 2% and 15% by weight.

28. A method according to claim 25, wherein the temperature in the extractive distillation and aromatics rectification is from 50° C. to 180° C.

* * * * *